US012633775B2

(12) United States Patent
Javich et al.

(10) Patent No.: US 12,633,775 B2
(45) Date of Patent: May 19, 2026

(54) BIDIRECTIONAL WIRELESS DATA AND POWER TRANSFER OVER INDUCTIVE LINK

(71) Applicant: Nia Therapeutics, Inc., Radnor, PA (US)

(72) Inventors: Aleksey Javich, Katy, TX (US); Christopher Brian Jensen, Sugar Land, TX (US); Satyajit Ketkar, Katy, TX (US); Randolph Armstrong, Katy, TX (US)

(73) Assignee: Nia Therapeutics, Inc., Radnor, PA (US)

( * ) Notice: Subject to any disclaimer, the term of this patent is extended or adjusted under 35 U.S.C. 154(b) by 0 days.

(21) Appl. No.: 18/856,452

(22) PCT Filed: Apr. 12, 2023

(86) PCT No.: PCT/US2023/065655
§ 371 (c)(1),
(2) Date: Oct. 11, 2024

(87) PCT Pub. No.: WO2023/201246
PCT Pub. Date: Oct. 19, 2023

(65) Prior Publication Data
US 2025/0293545 A1 Sep. 18, 2025

Related U.S. Application Data

(60) Provisional application No. 63/362,928, filed on Apr. 13, 2022.

(51) Int. Cl.
H02J 50/10 (2016.01)
A61N 1/372 (2006.01)
(Continued)

(52) U.S. Cl.
CPC .......... H02J 50/10 (2016.02); A61N 1/37223 (2013.01); A61N 1/3787 (2013.01); H03F 3/2176 (2013.01); H04L 27/02 (2013.01)

(58) Field of Classification Search
CPC ... H02J 50/10; A61N 1/37223; A61N 1/3787; H03F 3/2176; H04L 27/02
(Continued)

(56) References Cited

U.S. PATENT DOCUMENTS

| | | | |
|---|---|---|---|
| 8,385,461 B1* | 2/2013 | Pettus | H04L 27/04 375/259 |
| 9,246,554 B2* | 1/2016 | Maguire | H02J 50/40 |

(Continued)

OTHER PUBLICATIONS

International Search Report and Written Opinion issued in PCT/US2023/065655, mailed Oct. 13, 2023, 8 pages.
(Continued)

*Primary Examiner* — Alfonso Perez Borroto
(74) *Attorney, Agent, or Firm* — Morgan, Lewis & Bockius LLP

(57) ABSTRACT

Apparatus and methods for transferring both power and data across an inductive link using coupled coils are disclosed. In some embodiments, a disclosed apparatus comprises: an external device and an internal device. The external device comprises: a first LC tank comprising a first coil, a switching power amplifier comprising a first switch electrically coupled to the first LC tank, and a first data modulator configured to implement on-off keying (OOK) to open and close the first switch. The internal device comprises: a second LC tank comprising a second coil that is inductively coupled to the first coil through an inductive link, a tank circuit comprising a second switch electrically coupled to the second LC tank, and a second data modulator configured to implement cyclic on-off keying (COOK) to open and close the second switch.

19 Claims, 11 Drawing Sheets

(51) Int. Cl.
    *A61N 1/378*          (2006.01)
    *H03F 3/217*          (2006.01)
    *H04L 27/02*          (2006.01)

(58) Field of Classification Search
    USPC ........................................................ 307/104
    See application file for complete search history.

(56) References Cited

U.S. PATENT DOCUMENTS

| | | | | |
|---|---|---|---|---|
| 9,294,154 | B2 * | 3/2016 | Ghovanloo | H04B 5/26 |
| 9,474,031 | B1 * | 10/2016 | Sedzin | H04W 52/243 |
| 9,929,584 | B2 * | 3/2018 | Aghassian | H02J 7/0047 |
| 10,003,862 | B2 * | 6/2018 | Rowland | H04Q 9/00 |
| 2005/0131494 | A1 * | 6/2005 | Park | A61N 1/37276 |
| | | | | 607/60 |
| 2008/0266014 | A1 * | 10/2008 | Ma | H04L 27/34 |
| | | | | 332/103 |
| 2011/0264945 | A1 * | 10/2011 | Tsai | G06F 1/266 |
| | | | | 713/340 |
| 2015/0110224 | A1 * | 4/2015 | Kang | H04L 27/04 |
| | | | | 375/300 |
| 2015/0256369 | A1 * | 9/2015 | Park | H03K 7/02 |
| | | | | 332/116 |
| 2016/0072301 | A1 * | 3/2016 | Maniktala | H04B 5/79 |
| | | | | 307/104 |
| 2017/0118543 | A1 * | 4/2017 | Ha | H04B 5/24 |
| 2019/0386703 | A1 * | 12/2019 | Rajapaksha | H04L 27/04 |

OTHER PUBLICATIONS

Trigui Aref et al., "Maximizing Data Transmission Rate for Implantable Devices Over a Single Inductive Link: Methodological Review", IEEE Reviews in Biomedical Engineering, vol. 12, pp. 72-87, XP011710339, ISSN: 1937-3333, DOI: 10.1109/RBME.2018.2873817.

Extended European Search Report in Application No. 23789119.7 dated Jan. 26, 2026, 13 pages.

* cited by examiner

OOK reverse data demodulation

620

621 IDLE

SYNC DETECTED

622 CHECK TIME SLOT FOR BITS: 00

NEXT

623 CHECK TIME SLOT FOR BITS: 01

NEXT

624 CHECK TIME SLOT FOR BITS: 10

NEXT

625 CHECK TIME SLOT FOR BITS: 11

NEXT

626 SAVE 8-BIT TO FIFO

NOT 8-BIT YET

DONE

OOK forward data modulation

610

612 IDLE

614 SPLIT INTO 2-BIT SEQUENCE

616 STOP CARRIER FOR ONE CYCLE AMONG 12 CLK CYCLES

FRAME NOT DONE

618 NEXT BYTE FROM FIFO

FRAME DONE

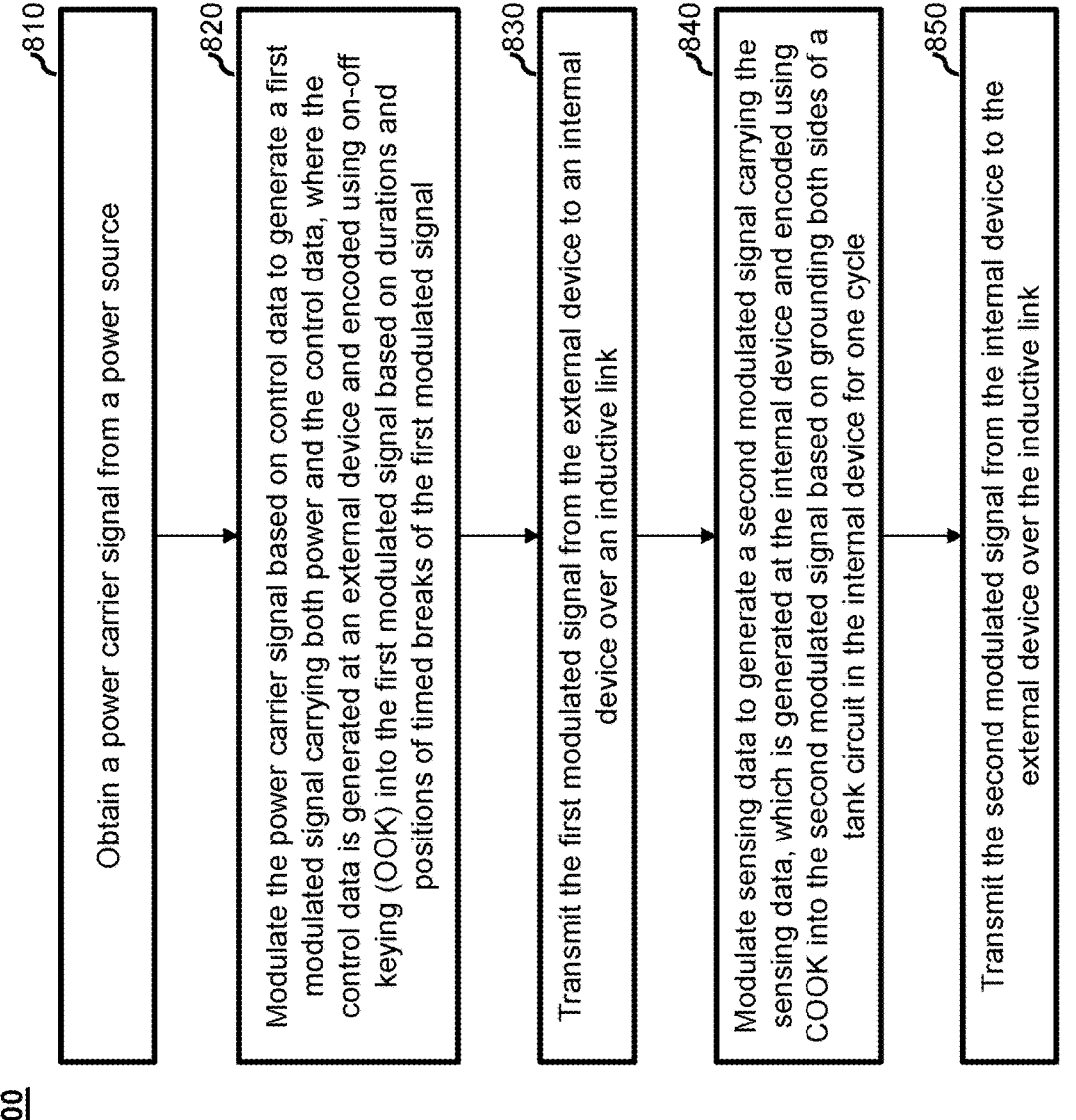

810 — Obtain a power carrier signal from a power source

820 — Modulate the power carrier signal based on control data to generate a first modulated signal carrying both power and the control data, where the control data is generated at an external device and encoded using on-off keying (OOK) into the first modulated signal based on durations and positions of timed breaks of the first modulated signal 830 — Transmit the first modulated signal from the external device to an internal device over an inductive link 840 — Modulate sensing data to generate a second modulated signal carrying the sensing data, which is generated at the internal device and encoded using COOK into the second modulated signal based on grounding both sides of a tank circuit in the internal device for one cycle 850 — Transmit the second modulated signal from the internal device to the external device over the inductive link

BIDIRECTIONAL WIRELESS DATA AND POWER TRANSFER OVER INDUCTIVE LINK

CROSS-REFERENCE TO RELATED APPLICATIONS

This application is a 371 National Entry of International Application No. PCT/US2023/065655, filed Apr. 12, 2023, and entitled "BIDIRECTIONAL WIRELESS DATA AND POWER TRANSFER OVER INDUCTIVE LINK," which claims priority to U.S. Provisional Patent Application No. 63/362,928, filed Apr. 13, 2022, and entitled "BIDIREC-TIONAL WIRELESS DATA AND POWER TRANSFER OVER INDUCTIVE LINK," all of which are incorporated herein in their entirety by reference.

TECHNICAL FIELD

This application relates generally to data and power transfer and, more particularly, to systems and methods for transferring both power and data across an inductive link using coupled coils.

BACKGROUND

Implantable medical devices can monitor, diagnose, and provide therapy to treat numerous health conditions. Many implantable devices use wireless technology to perform the dual functions of supplying power and providing data communication. While data and power can be respectively transferred over separate wireless links, many applications nowadays desire a single link to transfer both data and power wirelessly.

There are many challenges when creating an implantable device. Issues such as reliable and fast bidirectional data communication, efficient power delivery to the implantable circuits, low noise and low power for the recording part of the system, and delivery of safe stimulation to avoid tissue and electrode damage are some of the challenges faced by the microelectronics circuit designer. Although major advances have been achieved in the field of wireless communications and wireless powering for implanted devices, further improvements in terms of new and more suitable techniques that allow better optimization of the entire system are still needed.

SUMMARY

The embodiments described herein are directed to systems and methods for transferring both power and data across an inductive link using coupled coils in a bidirectional or unidirectional manner.

In one embodiment, a disclosed apparatus comprises: an external device and an internal device. The external device comprises: a first LC tank comprising a first coil, a switching power amplifier comprising a first switch electrically coupled to the first LC tank, and a first data modulator configured to implement on-off keying (OOK) to open and close the first switch. The internal device comprises: a second LC tank comprising a second coil that is inductively coupled to the first coil through an inductive link, a tank circuit comprising a second switch electrically coupled to the second LC tank, and a second data modulator configured to implement cyclic on-off keying (COOK) to open and close the second switch.

In another embodiment, a disclosed system comprises: an external device and an internal device. The external device comprises: a first LC tank comprising a first coil, a class E amplifier comprising a first switch electrically coupled to the first LC tank, and a first field programmable gate array (FPGA) configured to implement on-off keying (OOK) to open and close the first switch. The internal device comprises: a second LC tank comprising a second coil that is inductively coupled to the first coil through an inductive link, a tank circuit comprising a second switch electrically coupled to the second LC tank, and a second FPGA configured to implement cyclic on-off keying (COOK) to open and close the second switch.

In a different embodiment, a method is disclosed. The method comprises: obtaining a power carrier signal from a power source; modulating the power carrier signal based on control data to generate a first modulated signal carrying both power and the control data, wherein the control data is generated at an external device and encoded using on-off keying (OOK) into the first modulated signal based on durations and positions of timed breaks of the first modulated signal; transmitting the first modulated signal from the external device to an internal device over an inductive link; modulating sensing data to generate a second modulated signal carrying the sensing data, which is generated at the internal device and encoded using COOK into the second modulated signal based on grounding both sides of a tank circuit in the internal device for one cycle; transmitting the second modulated signal from the internal device to the external device over the inductive link.

BRIEF DESCRIPTION OF THE DRAWINGS

The features and advantages of the present invention will be more fully disclosed in, or rendered obvious by the following detailed description of the preferred embodiments, which are to be considered together with the accompanying drawings wherein like numbers refer to like parts and further wherein:

FIG. 8 is a flowchart illustrating an exemplary method for transferring both power and data across an inductive link, in accordance with some embodiments of the present teaching.

DETAILED DESCRIPTION

Figure 1:
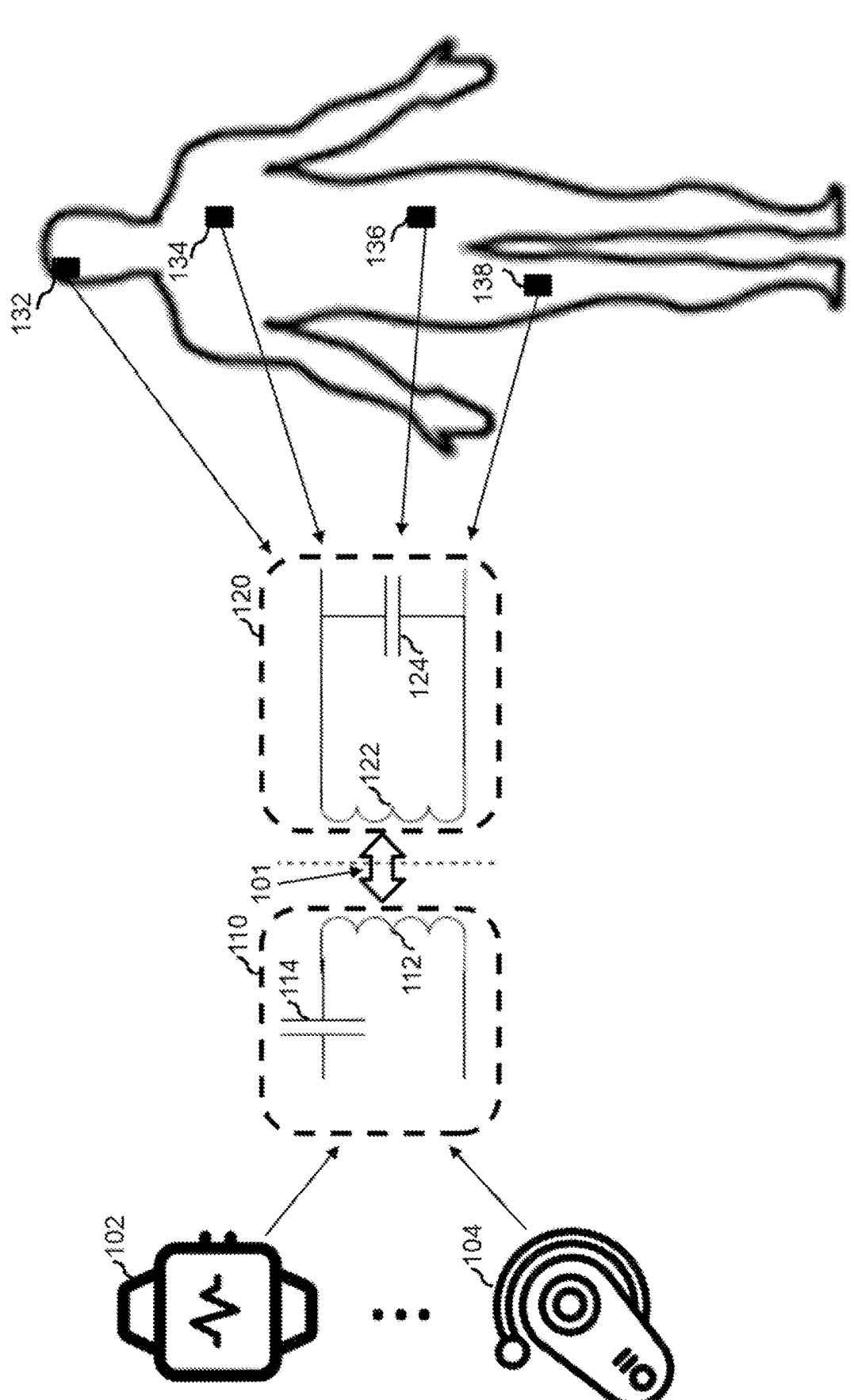
FIG. 1 shows various exemplary use cases for transferring both power and data across an inductive link, in accordance with some embodiments of the present teaching.

In the following, various embodiments are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the systems.

With the proliferation of power and form-factor constrained devices like implanted medical devices, radiofrequency identification (RFID) and wireless sensors, it is desirable to transfer both data and power wirelessly over a single link. The present teaching discloses systems and methods to provide inductively coupled power from a transmitter to a receiver while simultaneously allowing extremely high-speed data responses from the receiver back to the transmitter. In addition, the transmitter may transfer data to the receiver. That is, the transmitter may be a power and data transmitter. The receiver is a power and data receiver, and as well as a data responder.

In some embodiments, the receiver may be located at an internal device, e.g. within an implantable medical device that may be wholly or partially implanted into a human body. In some embodiments, the transmitter may be located at an external device, e.g. within a wearable device placed near the receiver.

In some embodiments, a coil in the internal device is inductively coupled to another coil in the external device. Both data and power can be transferred through the inductive link between the two coupled coils, in either an external-to-internal direction or an internal-to-external direction. In some use cases, e.g. an implanted medical device paired with a wearable device, power is transferred unidirectionally from the wearable device to the implanted medical device over the inductive link. While data is transferred bidirectionally in both directions, most data, e.g. sensing data generated by the implanted medical device based on monitoring a corresponding part of the human body, is transferred from the implanted medical device to the wearable device over the inductive link. But the wearable device also transfers some control data over the inductive link.

Due to different data and power transfer requirements in different directions, the external device and the internal device may include different components, modules and structures. In addition, the external device and the internal device may use different methods to modulate and demodulate data, to be suitable to their respective data transfer requirements.

The disclosed inductive power transfer system can achieve a data transfer symbol rate greater than 1% of the power transfer carrier frequency. In some embodiments, the data transfer symbol rate can be greater than 25% of the power transfer carrier frequency. In some embodiments, the data transfer symbol rate can be nearly 100% of the power transfer carrier frequency.

Furthermore, in the following, various embodiments are described with respect to methods and systems for transferring both power and data across an inductive link using coupled coils. In some embodiments, a disclosed apparatus comprises: an external device and an internal device. The external device comprises: a first LC tank comprising a first coil, a switching power amplifier comprising a first switch electrically coupled to the first LC tank, and a first data modulator configured to implement on-off keying (OOK) to open and close the first switch. The internal device comprises: a second LC tank comprising a second coil that is inductively coupled to the first coil through an inductive link, a tank circuit comprising a second switch electrically coupled to the second LC tank, and a second data modulator configured to implement cyclic on-off keying (COOK) to open and close the second switch.

Turning to the drawings, FIG. 1 shows various exemplary use cases for transferring both power and data across an inductive link, in accordance with some embodiments of the present teaching. An implantable medical device may be surgically placed inside a human body to treat, diagnose, or monitor medical conditions. Implantable medical devices are used to help regulate bodily functions, alleviate pain, or provide other therapeutic benefits. These devices can be wholly or partially implanted in the human body and can include things like: an implanted neural stimulator 132 implanted at the brain, a cardiac pacemaker 134 implanted at the heart, a drug delivery device 136 implanted at the abdomen, a foot drop implant device 138 implanted at the leg.

While each of these implantable medical devices can greatly improve the quality of life for patients, after being implanted into human body, many of these implantable medical devices need to send out lots of data with a limited size for storing any power. In some examples, only a small battery can be included in the implantable medical device, due to the limited size of the implantable medical device. In some examples, there is no battery in the implantable medical device. In either case, each implantable medical device would need to obtain power from external, e.g. a corresponding external device, to maintain its functions for a long enough time period. For example, the external device may be a wearable device 102, 104 placed on the human body, e.g. on the wrist, on the ear, or anywhere close enough to transfer power to the corresponding implantable medical device.

In some embodiments, each implantable medical device may be paired with a corresponding wearable device, which can transfer power as well as some control data to the implantable medical device over an inductive link, while the implantable medical device may send sensing or monitoring data to the corresponding wearable device over the same inductive link. For example, the implantable medical device 132 may be paired with the corresponding wearable device 104.

In the example shown in FIG. 1, each wearable device, e.g. the wearable device 104, may include a first LC circuit 110, while the corresponding implantable medical device, e.g. the implantable medical device 132, may include a second LC circuit 120. As shown in FIG. 1, the first LC circuit 110 comprises a coil inductor 112 and a capacitor 114; while the second LC circuit 120 comprises a coil inductor 122 and a capacitor 124. For each pair of wearable device and corresponding implantable medical device, the coil inductor 112 and the coil inductor 122 are inductively coupled to each other via the inductive link 101.

In some embodiments, the inductive link 101 may transfer data and power in both directions. The wearable device may be placed near the corresponding implantable medical device to ensure a good power and data transfer rate.

In some examples, a complete neural stimulator apparatus may include both an external device (e.g. the external device 104 wearable on an ear) and an internal device (e.g. the implanted neural stimulator 132 implanted at the brain). The external device 104 may communicate data with, and deliver power to, the implanted neural stimulator 132 over the inductive link 101. The implanted neural stimulator 132 is capable of recording and stimulating the brain; while the paired external device 104 may contain the neural data processing algorithms, as well as the power source.

This inductive link may allow for the implantable medical device to function without the need for any implanted battery, considerably improving the safety and size of the implantable medical device. While providing power, the inductive link may also serve as a communication platform, carrying the neural data from the implantable medical device to the external device. This neural data may be processed into a stimulation response, which may be transmitted back to the implantable medical device through the inductive link. This call and response style of communication (half-duplex) may be encoded such that the communication is net bidirectional, while being only in one direction at any one moment.

Figure 2:
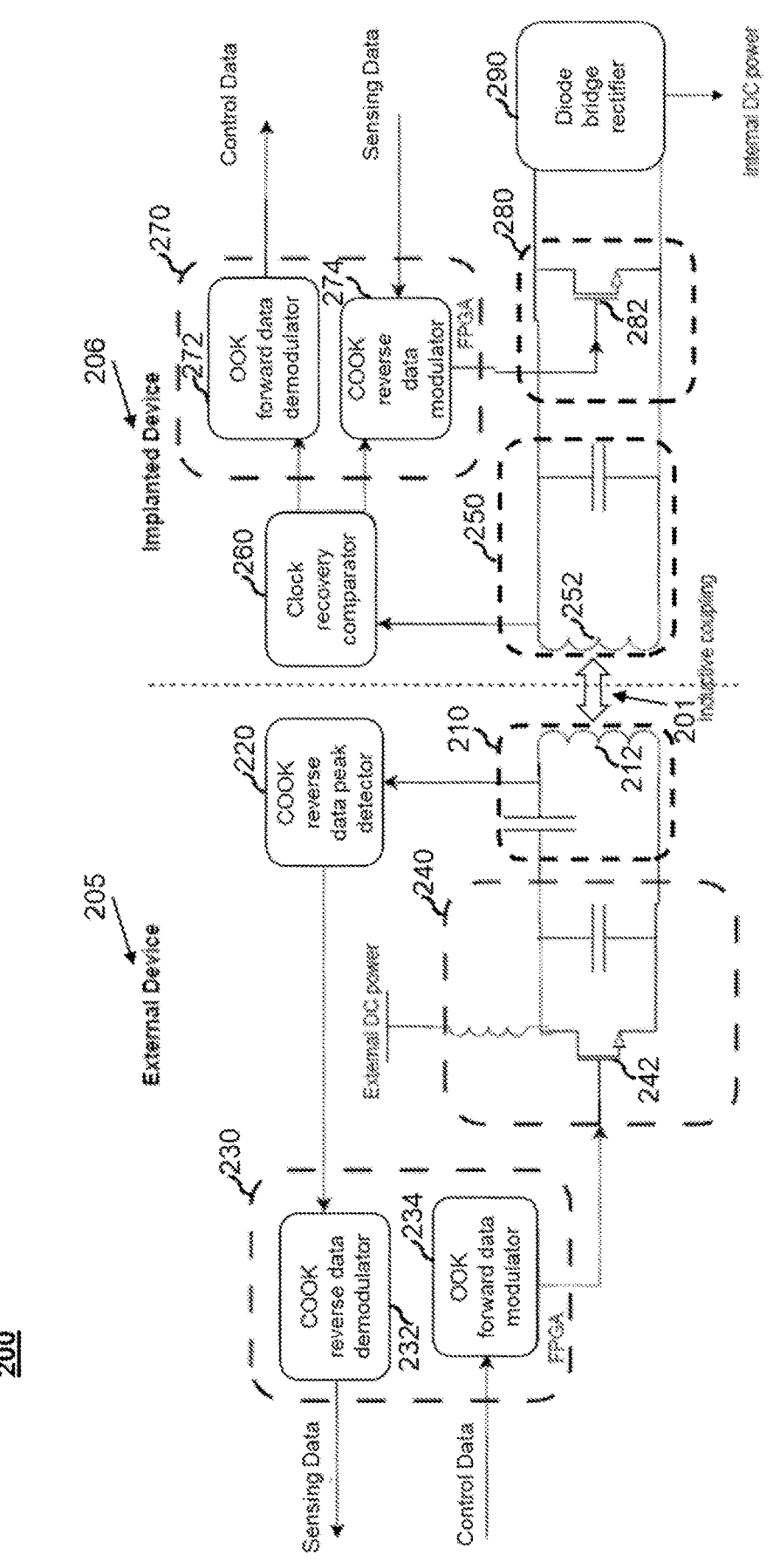
FIG. 2 is an exemplary system block diagram for transferring both power and data across an inductive link, in accordance with some embodiments of the present teaching.

FIG. 2 is an exemplary system block diagram of an apparatus 200 for transferring both power and data across an inductive link, in accordance with some embodiments of the present teaching. As shown in FIG. 2, the apparatus 200 includes an external device 205 and a corresponding paired implanted device 206. In some embodiments, the external device 205 may be any of the wearable devices 102~104 in FIG. 1, while the corresponding paired implanted device 206 may be any of the implantable medical devices 132~138 in FIG. 1.

The external device 205 and the implanted device 206 can communicate data to each other via an inductive coupling link 201 in both directions, while the external device 205 can also transfer power to the implanted device 206 via the inductive coupling link 201. In some examples, the data transferred from the external device 205 to the implanted device 206 is referred to as forward data, while the data transferred back from the implanted device 206 to the external device 205 is referred to as reverse data.

In some examples, the forward data may be modulated based on on-off keying (OOK), where the power carrier signal has timed breaks, and the forward data can be carried and recovered by locations and durations of these breaks in the carrier signal. In some examples, the reverse data may be modulated in a much different manner than the forward data. For example, the reverse data may be modulated based on cyclic on-off keying (COOK), where a reflected voltage change on the external device 205 can be induced by a temporary disruption of the induced oscillating voltage. In some embodiments, the COOK based modulation may follow a time-encoded symbol mapping scheme and may be effected for a single cycle of the carrier frequency. In some embodiments, this voltage change may be induced through grounding both sides of the tank circuit for one cycle, which can make the voltage drop on the external side. The voltage change can be extracted and read as a 1 or 0. In some embodiments, the COOK encoding may map this 1 to one of three possible locations in the waveform, resulting in one of four potential symbols sent at a time.

As shown in FIG. 2, the external device 205 includes: a first LC tank 210 comprising a first coil 212, a switching power amplifier 240 comprising a first switch 242 electrically coupled to the first LC tank 210, and a first field programmable gate array (FPGA) 230. The switching power amplifier 240 may be configured to obtain a power carrier signal from an external power source, e.g. an external DC power, and drive the first switch 242 based on a first modulated signal.

The switching power amplifier 240 may be a class E amplifier, a class D amplifier, another oscillating driver, according to various embodiments. The selection of coil drivers for implementing the switching power amplifier 240 on the external device 205 may depend on an operation frequency range of the external device 205, data rate requirement, efficiency requirement, etc.

As shown in FIG. 2, the first FPGA 230 comprises an OOK forward data modulator 234 and a COOK reverse data demodulator 232. In some embodiments, the OOK forward data modulator 234 is configured to implement on-off keying (OOK) to open and close the first switch 242. The OOK forward data modulator 234 may be configured to modulate the power carrier signal based on control data to generate the first modulated signal carrying both power and the control data. The control data may include any data related to instruction and control of the operations of the implanted device 206. In some embodiments, the control data is encoded using OOK into the first modulated signal based on durations and positions of timed breaks of the first modulated signal. The external device 205 may transmit the first modulated signal, carrying both power and the control data, to the implanted device 206 over the inductive coupling link 201.

In some embodiments, the switching power amplifier 240 receives an adjustable power supply from the external power source to allow variation in the generated magnetic field strength at the first coil 212. The power field frequency may be set by a clock input from the FPGA, e.g. at 8 MHz. Data transmission from the external device 205 may be modulated by amplitude-shift keying of the 8 MHz power clock in this example. The modulation is on-off keyed, such that inductive power is transferred from the external device 205 to the implanted device 206 by the coupled coils 212, 252, driven by the modulated signal.

As shown in FIG. 2, the implanted device 206 includes: a second LC tank 250 comprising a second coil 252, a tank circuit 280 comprising a second switch 282 electrically coupled to the second LC tank 250, and a second FPGA 270. The tank circuit 280 may be configured to drive the second switch 282 based on a second modulated signal.

As shown in FIG. 2, the second FPGA 270 comprises an OOK forward data demodulator 272 and a COOK reverse data modulator 274. In some embodiments, the COOK reverse data modulator 274 is configured to implement cyclic on-off keying (COOK) to open and close the second switch 282. The COOK reverse data modulator 274 may be configured to modulate sensing data to generate the second modulated signal carrying the sensing data. The sensing data may include any data obtained by the implanted device 206 by sensing or monitoring the corresponding part of the human body. In some embodiments, the sensing data is encoded using COOK into the second modulated signal based on grounding both sides of the tank circuit 280 for one cycle of the carrier signal. The implanted device 206 may transmit the second modulated signal, carrying the sensing data, to the external device 205 over the inductive coupling link 201.

In addition, the external device 205 further comprises a COOK reverse data peak detector 220 configured to detect peaks of a voltage signal at the first LC tank 210. The voltage signal reflects a voltage change induced by the second modulated signal transferred from the implanted device 206. The COOK reverse data demodulator 232 in this example may be configured to demodulate, based on the detected peaks, the sensing data carried by the voltage signal with reflected voltage change. For example, after receiving the detected peaks, the COOK reverse data demodulator 232 may determine waveform edges to demodulate bit 1 or bit 0, based on synchronization and timing of the detected peaks.

As shown in FIG. 2, the implanted device 206 further comprises: a clock recovery comparator 260 configured to convert an analog signal at the second LC tank 250 to a digital signal. The digital signal may serve as a clock signal for both the OOK forward data demodulator 272 and the COOK reverse data modulator 274. The OOK forward data demodulator 272 may be configured to demodulate the control data based on the digital signal. In addition, the implanted device 206 further comprises a diode bridge rectifier 290 configured to capture and rectify the power transmitted from the external device 205 over the inductive coupling link 201. The diode bridge rectifier 290 may send the power to different components of the implanted device 206 as an internal DC power. In some embodiments, when the diode bridge rectifier 290 includes a chargeable battery, the diode bridge rectifier 290 may store the power in the battery.

In some embodiments, the diode bridge rectifier 290 is a passive rectifier without receiving any input from a phase-locked loop (PLL) or the clock recovery comparator 260. Actually, the apparatus 200 in this example does not include any PLL, thus reducing power consumption of the apparatus 200, especially reducing the power consumption of the implanted device 206. The clock recovery comparator 260 merely provides signals to the second FPGA 270. While a PLL processes analog signals, an FPGA processes digital signals, which are easy to control and change codes.

As shown in FIG. 2, each terminal side of the inductive coupling link 201 contains an antenna coil and a circuitry which serves to maintain a harmonic oscillation of the carrier signal. On the side of the implanted device 206, this may be the tank (inductor-capacitor/LC) circuit 280. On the side of the external device 205, this may be the switching power amplifier 240, which generates an alternating current. This alternating current may be generated on the external device 205 and may induce a current in the implanted device 206. This induced current may then be rectified and transformed to DC power at the implanted device 206.

In some embodiments, the power and data transmission of the apparatus 200 is based on the 8 MHz carrier signal, which is generated through the switching power amplifier 240. In some embodiments, the switching power amplifier 240 is a class E amplifier, which is power efficient oscillatory signal generator that actively switches phase when the voltage at the switch is zero. This may serve as an electric equivalent to a swinging pendulum, completing one full cycle at 8 MHz. The switching power amplifier 240 may include a gate to modulate this pendulum. In the absence of any data for transmission, the gate would switch at 16 MHz as the pendulum crosses 0 V. The control data may be encoded through prolonged switch activation, cutting power added to the switching power amplifier 240 for a cycle. The duration and position of this pause encodes the control data based on OOK to be transmitted to the implanted device 206 over the inductive coupling link 201.

In the embodiments described above regarding FIG. 2, the apparatus 200 is capable of bidirectional (non-simultaneous) data transmission, with a singular power source located on the external side. While the tank circuit 280 is used on the implanted side, the switching power amplifier 240 is used on the external side for efficient signal generation. External to internal communication is encoded through position and duration of momentary carrier signal interruptions, called OOK. The OOK modulation is more suitable than COOK to the external to internal communication, due to a low data rate requirement for the external to internal communication. While OOK provides an efficient way of sending low bandwidth data to the implanted device 206 in the human body, COOK is used to modulate a high bandwidth data transfer out of the human body to the external device 205.

COOK is used to modulate the second coil 252 by turning on or off the second switch 282 in synchronization with the carrier signal, meaning the second switch 282 is turned on only when the carrier signal goes high, or only when the carrier signal goes low. OOK, on the other hand, can be used to modulate the first coil 212 by turning on the first switch 242 whenever desired, meaning the first switch 242 is turned on whenever there is control data to send, regardless of the waveform phase of the first coil 212.

Various alternative embodiments can be based on FIG. 2, by replacing one or more components and/or one or more modulation/demodulation schemes. In a first alternative embodiment, one tank circuit may be implanted at the implanted device 206 for energy efficient power transmission, where COOK based encoding onto the waveform may be done through shorting both sides of the second LC tank 250 together for a single signal cycle. In this case, communication and power may each be transmitted unidirectionally.

In a second alternative embodiment, both the external and internal sides of the inductive link may include tank circuits with switches, to short their respective LC tank to transmit data. That is, the switching power amplifier 240 in this embodiment may be replaced by another tank circuit, to modulate the forward data based on COOK as well. While this approach allows for a theoretical bidirectional data transmission, it would require a power bank on the internal side to be capable of generating the carrier frequency.

In some alternative embodiments, the encoding schemes of either direction may be varied and remain an effective transmission tool. In some alternative embodiments, the OOK on the external side may be asynchronous; while in other alternative embodiments, the OOK on the external side may be synchronous in the data frame. A trade-off/use-case may exist in which increased bit rate in tandem with a decreased power transmission (or reverse) is acceptable. This variability may also be extended to frequency and amplitude of the carrier signal.

In some alternative embodiments, the hardware (component-level) modulating the tank circuit on the internal device may be varied. Performance would not be significantly impacted provided the hardware is still able to reflect change onto the external LC tank and receive power. In some alternative embodiments, the coil characteristics such as shape, quality factor, core/backing material may change.

Figure 3A:
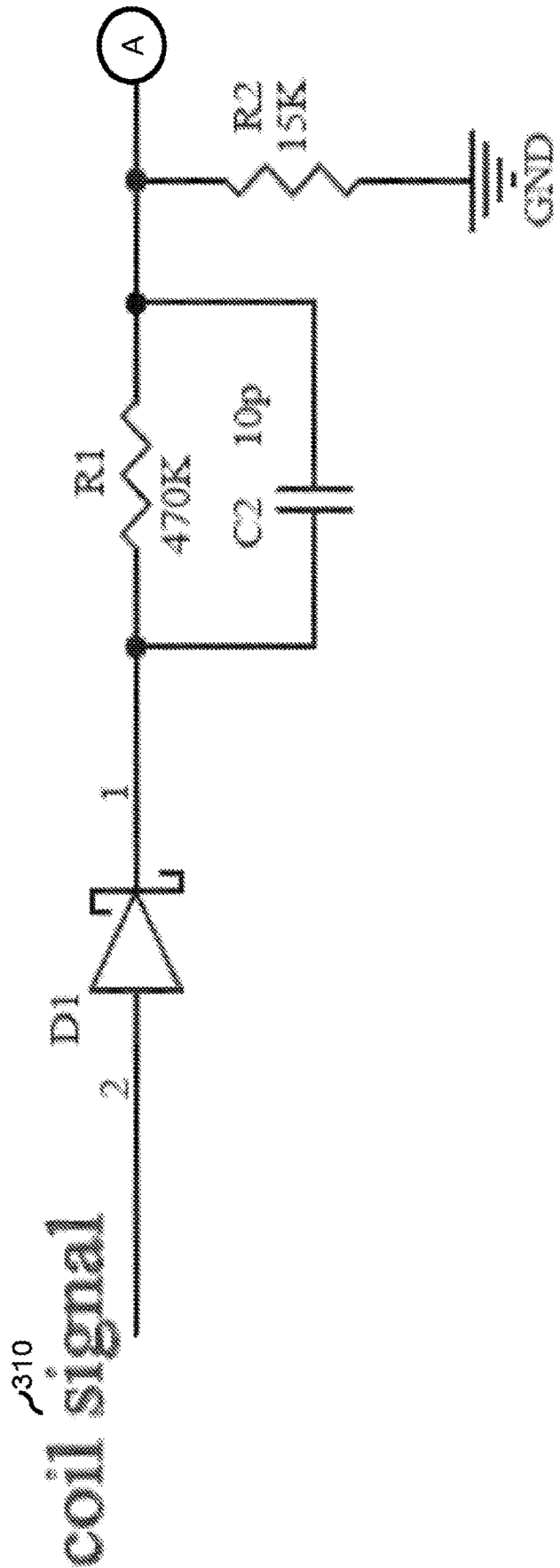
FIG. 3A and FIG. 3B show a circuit schematic for an exemplary clock recovery comparator in an internal device for wireless data and power transfer, in accordance with some embodiments of the present teaching.
Figure 3B:
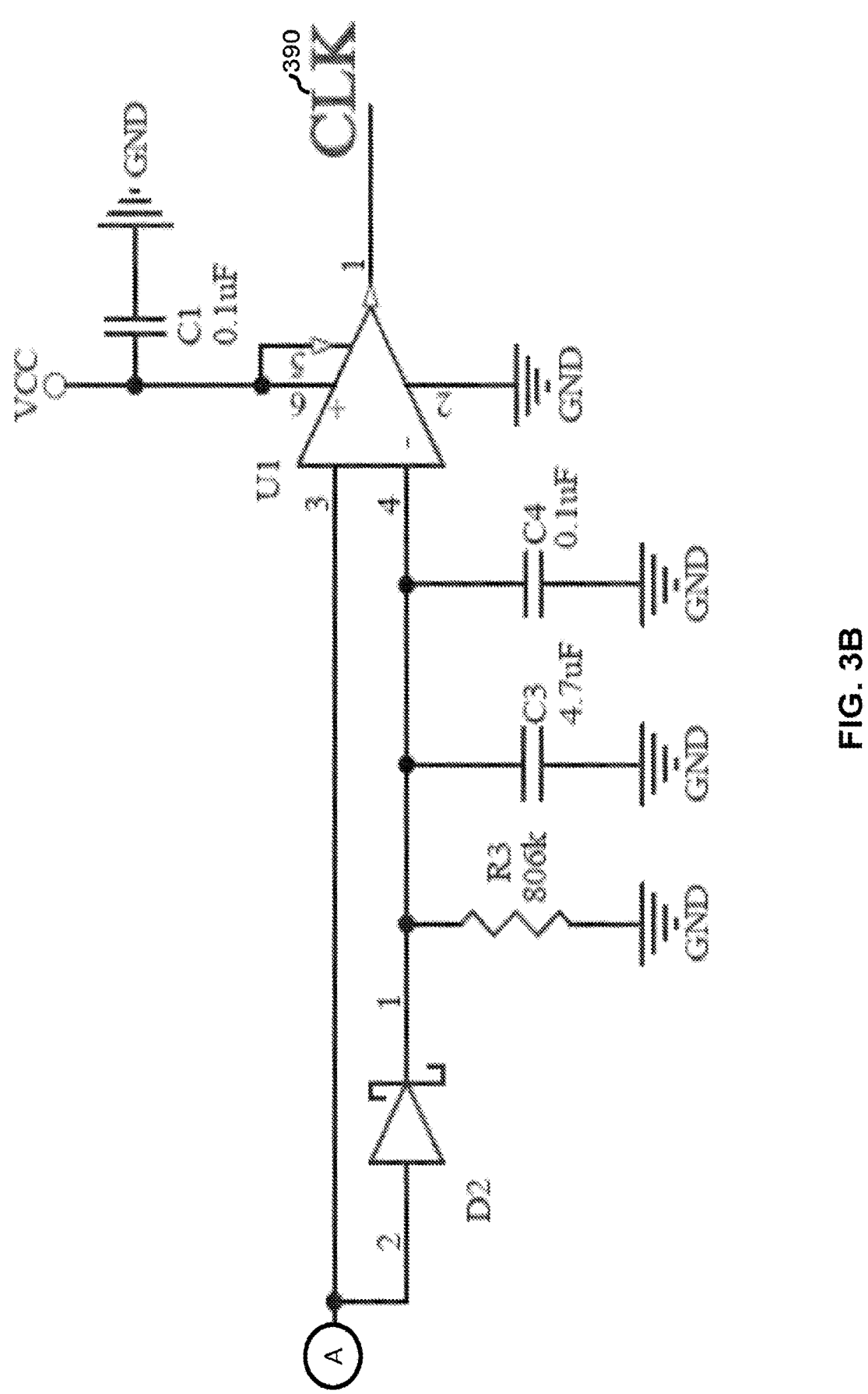

FIG. 3A and FIG. 3B show a circuit schematic for an exemplary clock recovery comparator in an internal device for wireless data and power transfer, in accordance with some embodiments of the present teaching. In some embodiments, the exemplary clock recovery comparator shown in FIG. 3 may be the clock recovery comparator 260 in FIG. 2.

As indicated in FIG. 3A and FIG. 3B, the clock recovery comparator can monitor a coil signal 310 obtained from a coupled coil, to decode the power transmitter data as a clock signal CLK 390. While the coil signal 310 is an analog signal, the CLK 390 is a digital signal. In some embodiments, the clock recovery comparator recovers a 8 MHz clock signal out of the sinusoidal waveform of the coil signal 310. In some embodiments, the clock recovery comparator masks out the clock signal when the second switch 282 is switched off, to prevent the clock from stopping when the coil signal 310 stops.

In some embodiments, the coil signal 310 may be obtained from the second coil 252 in FIG. 2, and can carry both power and control data transferred from the external device 205 over the inductive coupling link 201. In some embodiments, the CLK 390 can serve as a digital clock signal for the second FPGA 270. Based on the digital clock signal, the COOK reverse data modulator 274 in the second FPGA 270 can generate high-speed data responses, to be encoded as load-shift keying on the second coil 252, which may be detected in the reflected impedance of the first coil 212.

In the example shown in FIG. 3A and FIG. 3B, the clock recovery comparator includes a diode D1 receiving and forwarding the coil signal 310 to an RC circuit including a resistor R1 connected to a capacity C2 in parallel. The output of the RC circuit is shorted to the V+ input of a comparator U1, where a circuit portion including diode D2, resistors R2, R3, and capacitors C3, C4, is connected between the output of the RC circuit and the V− input of the comparator U1. The comparator U1 outputs the digital signal CLK 390. The values and units shown in FIG. 3A and FIG. 3B for different components are for illustrative purposes, without limiting the scope of the present teaching.

Figure 4A:
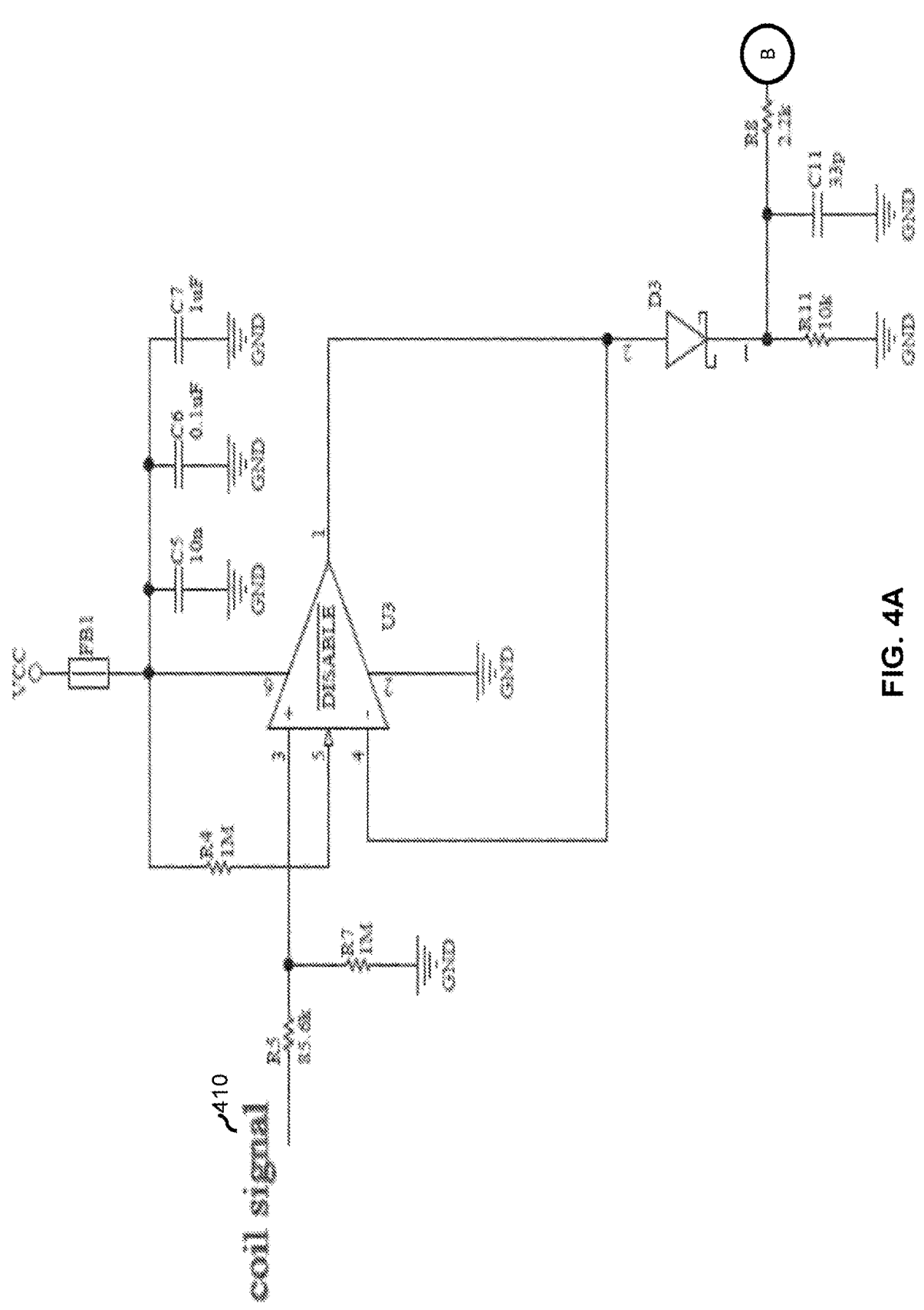
FIG. 4A and FIG. 4B show a circuit schematic for an exemplary data peak detector in an external device for wireless data and power transfer, in accordance with some embodiments of the present teaching.
Figure 4B:
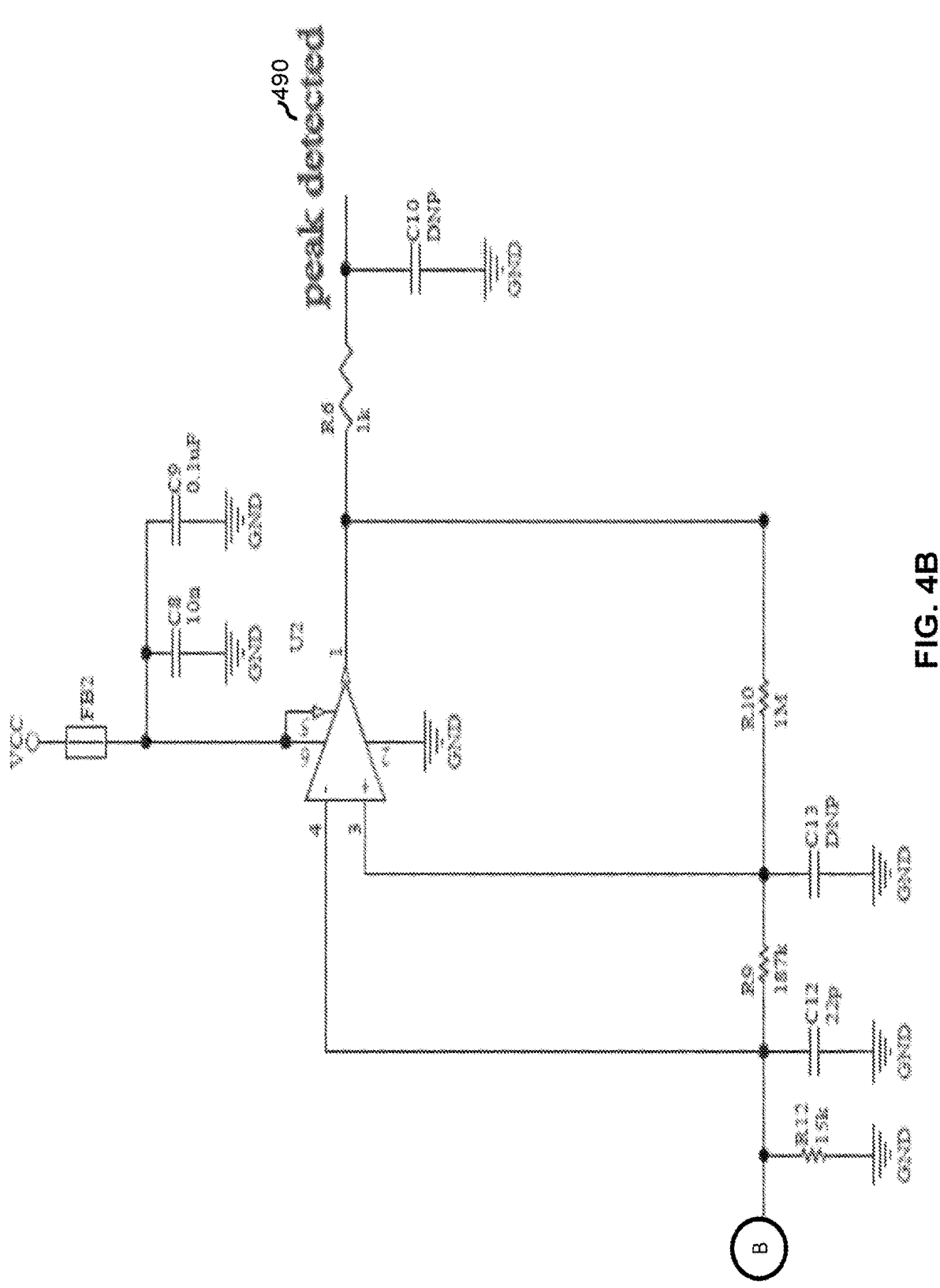

FIG. 4A and FIG. 4B show a circuit schematic for an exemplary data peak detector in an external device for wireless data and power transfer, in accordance with some embodiments of the present teaching. In some embodiments, the exemplary data peak detector shown in FIG. 4A and FIG. 4B may be the COOK reverse data peak detector 220 in FIG. 2.

As indicated in FIG. 4A and FIG. 4B, the data peak detector can monitor a coil signal 410 obtained from a coupled coil, to detect peaks of the coil signal 410. In some embodiments, while the coil signal 410 is an analog signal, the data peak detector converts the coil signal 410 into a digital signal, the peak signal 490.

In some embodiments, the coil signal 410 may be obtained from the first coil 212 in FIG. 2, and can carry sensing data transferred from the implanted device 206 over the inductive coupling link 201 via reflected impedance modulation at the first coil 212. The peak signal 490 can capture extremely high-speed modulations, up to the power carrier frequency, of the sensing data. The peak signal 490 may represent the sensing data, e.g. the high-speed data responses generated by the second FPGA 270. In some embodiments, the peak signal 490 may be provided as an input to the FPGA, for sensing data demodulation. Based on the peak signal 490, the COOK reverse data demodulator 232 in the FPGA can demodulate the sensing data according to COOK.

In some embodiments, response data transfer symbol rates may be greater than or equal to 25% of the power transfer carrier frequency. In some embodiments, refinements using tuned components may achieve response data transfer symbol rate at 100% of the power transfer carrier frequency.

In the example shown in FIG. 4A and FIG. 4B, the data peak detector includes a buffer U3 receiving the coil signal 410 via a resistor R5. The output of the buffer U3 drives diode D3, whose output is connected to inputs of a comparator U2, through a circuit portion including resistors R8, R9, R11, R12, and capacitors C11, C12, C13. The comparator U2 outputs the peak signal 490, through a resistor R6. The values and units shown in FIG. 4A and FIG. 4B for different components are for illustrative purposes, without limiting the scope of the present teaching.

Figure 5A:
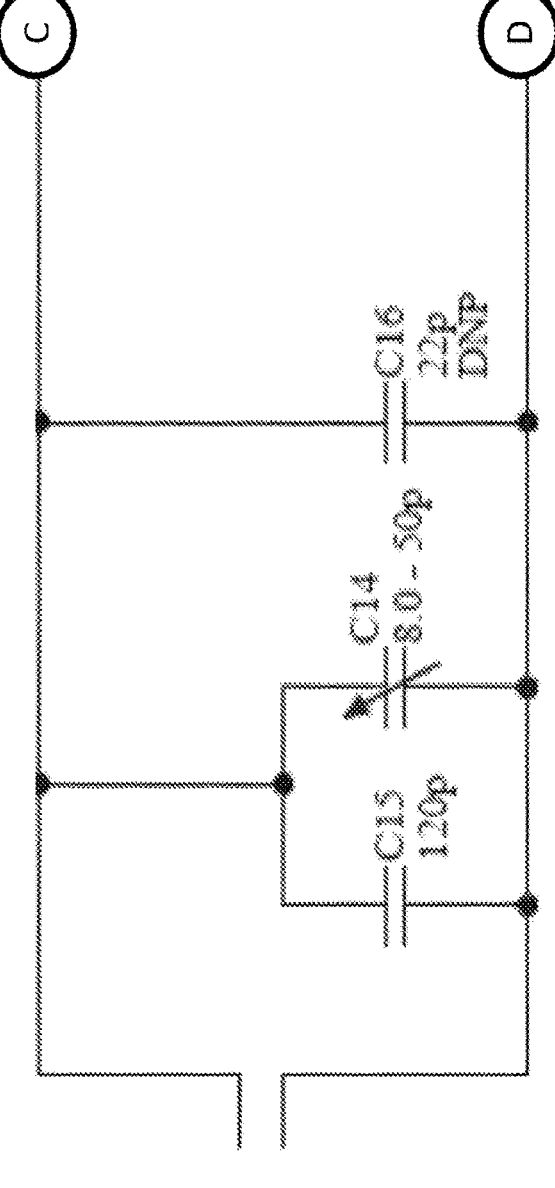
FIG. 5A and FIG. 5B show a circuit schematic for an exemplary diode bridge rectifier in an internal device for wireless data and power transfer, in accordance with some embodiments of the present teaching.
Figure 5B:
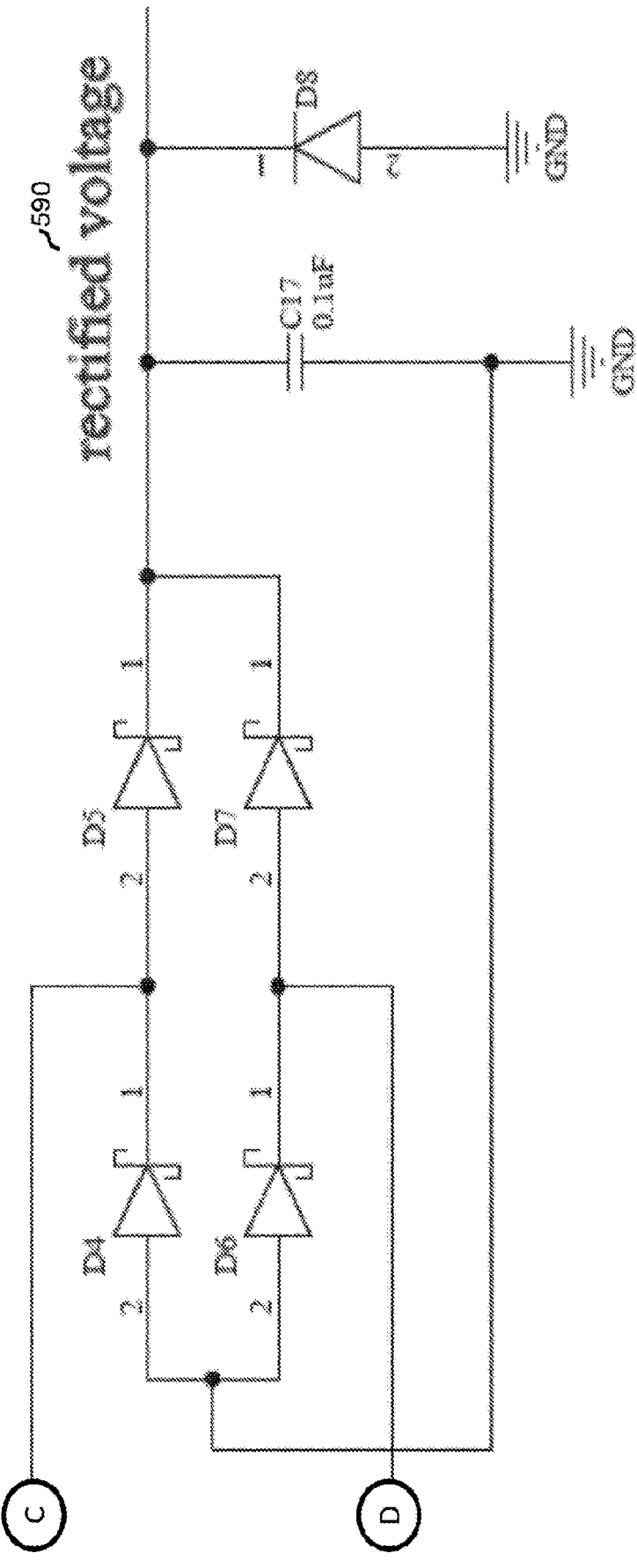

FIG. 5A and FIG. 5B a circuit schematic for an exemplary diode bridge rectifier in an internal device for wireless data and power transfer, in accordance with some embodiments of the present teaching. In some embodiments, the exemplary diode bridge rectifier shown in FIG. 5A and FIG. 5B may be the diode bridge rectifier 290 in FIG. 2. As indicated in FIG. 5A and FIG. 5B, the diode bridge rectifier can receive a power signal 510 obtained from a coupled coil, to rectify the power transmitted from the external device and capture the rectified voltage signal 590.

In some embodiments, the power signal 510 may be obtained from the second coil 252 in FIG. 2, and can carry power transferred from the external device 205 over the inductive coupling link 201. In some embodiments, the diode bridge rectifier may be a full wave rectifier that can rectify the waveform of the power signal 510, to deliver an appropriate supply voltage to various components and loads of the implanted device 206 via the rectified voltage signal 590. In some embodiments, the diode bridge rectifier can operate without any extra control signal.

In the example shown in FIG. 5A and FIG. 5B, the diode bridge rectifier includes a voltage capture circuit, including capacitors C14, C15, C16, which is configured to capture power from the power signal 510. The diode bridge rectifier further includes a diode bridge comprising four diodes D4, D5, D6, D7, connected back to back in a bridge configuration for rectification. The diode bridge receives the captured AC power, and converts the alternating current (AC) power signal 510 to a direct current (DC) power signal. The output of the diode bridge is connected to a smoothing capacitor C17 to clean the signal to prevent voltage spikes, thus generating a steady DC signal as the rectified voltage signal 590. The values and units shown in FIG. 5A and FIG. 5B for different components are for illustrative purposes, without limiting the scope of the present teaching.

In some embodiments, data may be extracted at the implanted device 206 by comparing found voltage vs. expected voltage of the carrier signal. The sensing data may be transmitted through modulating connection of both sides of the tank circuit 280 to ground. In some embodiments, a gate in the tank circuit 280 grounds the nodes of the coil 252, e.g. through the D5 diode in FIG. 5A and FIG. 5B. This temporary disruption of the induced oscillating voltage between the tank circuit nodes creates a reflection on the external coil 212, which carries the sensing data. In one example, the COOK scheme opens the gate for one out of every 7 cycles, and the cycle selected determines the 2-bit symbol transmitted. As both terminals are grounded, no power is recovered during COOK encoding, while the smoothing capacitor C17 begins to discharge to maintain output voltage levels. When power recovery resumes, the smoothing capacitor C17 is replenished.

In some embodiments, the various design options shown in FIGS. 2-5 can give a good combination of off-the-shelf components to make a feasible inductive link design product with a high quality-price-ratio.

Figure 6B:
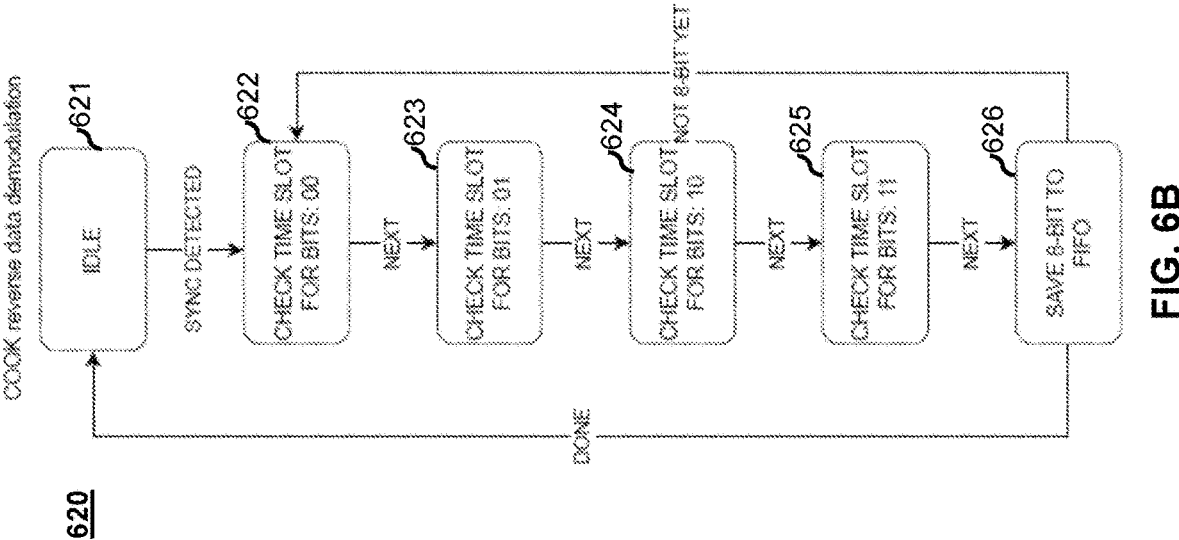
FIG. 6B is a flow chart illustrating a process for reverse data demodulation at an external device based on cyclic on-off keying (COOK), in accordance with some embodiments of the present teaching.
Figure 6A:
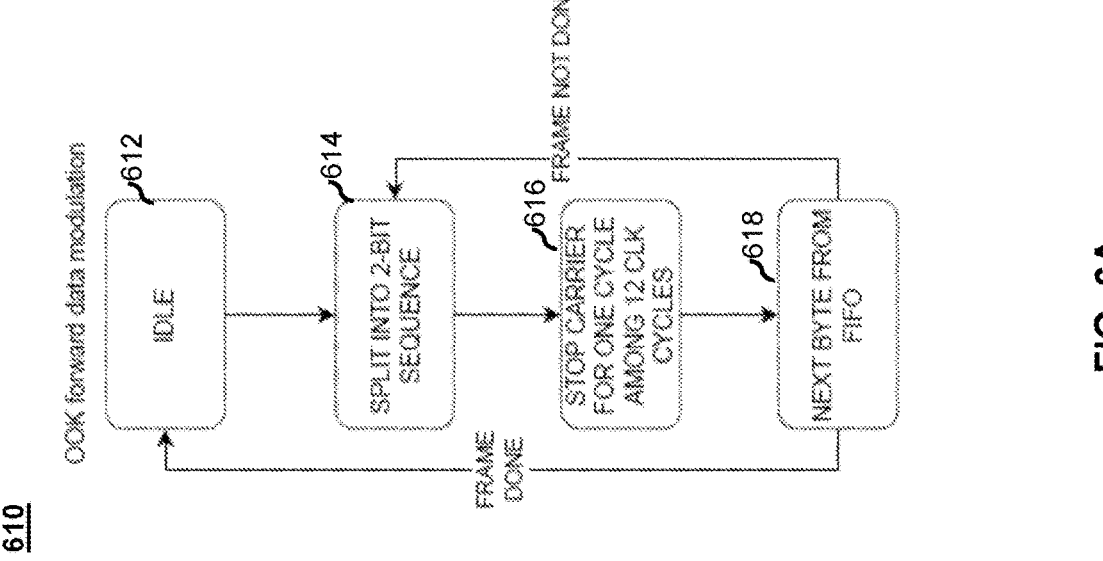
FIG. 6A is a flow chart illustrating a process for forward data modulation at an external device based on on-off keying (OOK), in accordance with some embodiments of the present teaching.

FIG. 6A is a flow chart illustrating a process 610 for forward data modulation at an external device based on on-off keying (OOK), in accordance with some embodiments of the present teaching. In some embodiments, the process 610 may be carried out by an external device, such as the external device 205 in FIG. 2. In some embodiments, the process 610 may be carried out by the OOK forward data modulator 234 in the external device 205.

As shown in FIG. 6A, the process 610 starts from operations 612, where the OOK forward data modulator 234 is at an idle state. At operation 614, the modulation starts, by splitting incoming data (e.g. a byte from a queue of control data) into 2-bit sequences. At operation 616, the carrier signal is stopped or turned off, for one cycle among every 12 cycles, to modulate the 2-bit sequences based on OOK. At operation 618, next byte from a first in first out (FIFO) queue is identified. If the entire data frame has been done for modulation, the process goes back to operation 612 to enter idle state. Otherwise, if the entire data frame has not been done for modulation, the process goes back to operation 614 to modulate next byte.

FIG. 6B is a flow chart illustrating a process 620 for reverse data demodulation at an external device based on cyclic on-off keying (COOK), in accordance with some embodiments of the present teaching. In some embodiments, the process 620 may be carried out by an external device, such as the external device 205 in FIG. 2. In some embodiments, the process 620 may be carried out by the COOK reverse data demodulator 232 in the external device 205.

As shown in FIG. 6B, the process 620 starts from operations 621, where the COOK reverse data demodulator 232 is at an idle state. At operation 622, after a synchronization signal is detected, e.g. based on a peak signal generated by the COOK reverse data peak detector 220, the demodulation starts, by checking time slot to demodulate bits "00." At operation 623, the time slot is checked to demodulate bits "01." At operation 624, the time slot is checked to demodulate bits "10." At operation 625, the time slot is checked to demodulate bits "11." At operation 626, the 8-bit data is saved into a FIFO queue. If all of the 8-bit have been demodulated, the process goes back to the operation 621 to enter an idle state. If not all 8-bit are demodulated yet, the process goes back to the operation 622 to re-check the time slots.

Figures 7A, 7B:
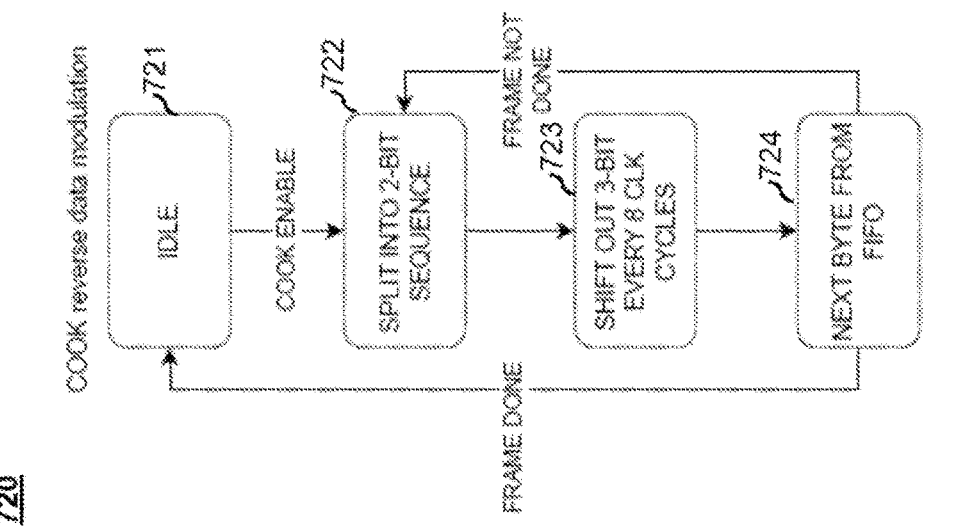
FIG. 7A is a flow chart illustrating a process for forward data demodulation at an internal device based on OOK, in accordance with some embodiments of the present teaching.
FIG. 7B is a flow chart illustrating a process for reverse data modulation at an internal device based on COOK, in accordance with some embodiments of the present teaching.

FIG. 7A is a flow chart illustrating a process 710 for forward data demodulation at an internal device based on OOK, in accordance with some embodiments of the present teaching. In some embodiments, the process 710 may be carried out by an internal device, such as the implanted device 206 in FIG. 2. In some embodiments, the process 710 may be carried out by the OOK forward data demodulator 272 in the implanted device 206.

As shown in FIG. 7A, the process 710 starts from operations 711, where the OOK forward data demodulator 272 is at an idle state. At operation 712, the demodulation starts, by waiting for a synchronization signal, e.g. based on the CLK signal generated by the clock recovery comparator 260. Once the synchronization signal is detected, at operation 713, the time slot is checked to demodulate bits "00." At operation 714, the time slot is checked to demodulate bits "01." At operation 715, the time slot is checked to demodulate bits "10." At operation 716, the time slot is checked to demodulate bits "11." At operation 717, the 8-bit data is saved into a FIFO queue. If all of the 8-bit have been demodulated, the process goes back to the operation 711 to enter an idle state. If not all 8-bit are demodulated yet, the process goes back to the operation 713 to re-check the time slots.

FIG. 7B is a flow chart illustrating a process 720 for reverse data modulation at an internal device based on COOK, in accordance with some embodiments of the present teaching. In some embodiments, the process 720 may be carried out by an internal device, such as the implanted device 206 in FIG. 2. In some embodiments, the process 720 may be carried out by the COOK reverse data modulator 274 in the implanted device 206.

As shown in FIG. 7B, the process 720 starts from operations 721, where the COOK reverse data modulator 274 is at an idle state. At operation 722, once COOK is enabled, e.g. based on sensing data generated at the implanted device 206, the modulation starts, by splitting incoming data (e.g. a byte from a queue of sensing data) into 2-bit sequences. At operation 723, the carrier signal is modulated such that 3 bits are shifted out for every 8 clock cycles, to modulate the 2-bit sequences based on COOK. At operation 724, next byte from a FIFO queue is identified. If the entire data frame has been done for modulation, the process goes back to operation 721 to enter idle state. Otherwise, if the entire data frame has not been done for modulation, the process goes back to operation 722 to modulate next byte.

FIG. 8 is a flowchart illustrating an exemplary method 800 for transferring both power and data across an inductive link, in accordance with some embodiments of the present teaching. In some embodiments, the method 800 can be carried out by an apparatus including an external device and an internal device, such as the apparatus 200 in FIG. 2. Beginning at operation 810, a power carrier signal is obtained from a power source. At operation 820, the power carrier signal is modulated based on control data to generate a first modulated signal carrying both power and the control data. The control data is generated at the external device and encoded using on-off keying (OOK) into the first modulated signal based on durations and positions of timed breaks of the first modulated signal. At operation 830, the first modulated signal is transmitted from the external device to the internal device over an inductive link, which is between the external device and the internal device.

At operation 840, sensing data is modulated to generate a second modulated signal carrying the sensing data, which is generated at the internal device and encoded using COOK into the second modulated signal based on grounding both sides of a tank circuit in the internal device for one cycle. At operation 850, the second modulated signal is transmitted from the internal device to the external device over the inductive link.

Although the methods described above are with reference to the illustrated flowcharts, it will be appreciated that many other ways of performing the acts associated with the methods can be used. For example, the order of some operations may be changed, and some of the operations described may be optional.

The embodiments described herein implement a methodology for bidirectional inductive links which can transmit data and power over short distances, such as those found in biomedical implants. The inductive link transmits bidirectional data, and unidirectional power from the external to the implanted components. The system achieves this through power transmission, power capture, two different means of data encoding/decoding, and recreation of synchronous system clock. This disclosure is generalizable to applications requiring wireless sensing and/or stimulation, in power or size constrained systems.

In some embodiments, the inductive link design described herein may be well suited for a wide range of biomedical implant recording technologies due to the data bandwidth. Additionally, the high-power transmission of the inductive link design may be well suited to implanted bio-stimulators. Where some wired power and data delivery to implanted devices may not be long-term stable due to infection, the embodiments described herein can communicate and transmit power inductively, safely passing through the skin. In addition, the embodiments described herein allow efficient wireless power transmission, and bidirectional data communication, capable of powering an electric stimulator, with enough bandwidth for neural data. For digital communications to implanted biomedical devices, the embodiments described herein eliminate the need for an independent power source, or additional data antenna on the internal side of the inductive communication.

In some embodiments, the methods and system described herein can be at least partially embodied in the form of computer-implemented processes and apparatus for practicing those processes. The disclosed methods may also be at least partially embodied in the form of tangible, non-transitory machine-readable storage media encoded with computer program code. For example, the steps of the methods can be embodied in hardware, in executable instructions executed by a processor (e.g., software), or a combination of the two. The media may include, for example, RAMs, ROMs, CD-ROMs, DVD-ROMs, BD-ROMs, hard disk drives, flash memories, or any other non-transitory machine-readable storage medium. When the computer program code is loaded into and executed by a computer, the computer becomes an apparatus for practicing the method. The methods may also be at least partially embodied in the form of a computer into which computer program code is loaded or executed, such that, the computer becomes a special purpose computer for practicing the methods. When implemented on a general-purpose processor, the computer program code segments configure the processor to create specific logic circuits. The methods may alternatively be at least partially embodied in application specific integrated circuits for performing the methods. In some embodiments, each functional component described herein can be implemented in computer hardware, in program code, and/or in one or more computing systems executing such program code as is known in the art.

The foregoing is provided for purposes of illustrating, explaining, and describing embodiments of these disclosures. Modifications and adaptations to these embodiments will be apparent to those skilled in the art and may be made without departing from the scope or spirit of these disclosures. Although the subject matter has been described in terms of exemplary embodiments, it is not limited thereto. Rather, the appended claims should be construed broadly, to include other variants and embodiments, which can be made by those skilled in the art.

The various drawings illustrate a number of elements in a particular order. However, elements that are not order dependent may be reordered and other elements may be combined or separated. While some reordering or other groupings are specifically mentioned, others will be obvious to those of ordinary skill in the art, so the ordering and groupings presented herein are not an exhaustive list of alternatives.

As used herein: the singular forms "a", "an," and "the" include the plural forms as well, unless the context clearly indicates otherwise; the term "and/or" encompasses all possible combinations of one or more of the associated listed items; the terms "first," "second," etc. are only used to distinguish one element from another and do not limit the elements themselves; the term "if" may be construed to mean "when," "upon," "in response to," or "in accordance with," depending on the context; and the terms "include," "including," "comprise," and "comprising" specify particular features or operations but do not preclude additional features or operations.

What is claimed is:

1. An apparatus, comprising:
an external device comprising:
a first LC tank comprising a first coil,
a switching power amplifier comprising a first switch electrically coupled to the first LC tank, wherein the switching power amplifier is configured to obtain a power carrier signal from an external power source, and
a first data modulator configured to implement on-off keying (OOK) to open and close the first switch, wherein the first data modulator is configured to modulate the power carrier signal based on control data to generate a first modulated signal carrying both power and the control data, wherein the control data is encoded using OOK into the first modulated signal based on durations and positions of timed breaks of the first modulated signal; and
an internal device comprising:
a second LC tank comprising a second coil that is inductively coupled to the first coil through an inductive link, wherein the first modulated signal is transmitted from the external device to the internal device over the inductive link,
a tank circuit comprising a second switch electrically coupled to the second LC tank, and
a second data modulator configured to implement cyclic on-off keying (COOK) to open and close the second switch.

2. The apparatus of claim 1, wherein:
the switching power amplifier is further configured to drive the first switch based on the first modulated signal.

3. The apparatus of claim 1, wherein:
the tank circuit is configured to drive the second switch based on a second modulated signal;
the second data modulator is configured to modulate sensing data to generate the second modulated signal carrying the sensing data;
the sensing data is encoded using COOK into the second modulated signal based on grounding both sides of the tank circuit for one cycle; and
the second modulated signal is transmitted from the internal device to the external device over the inductive link.

4. The apparatus of claim 3, wherein the external device further comprises:
a data peak detector configured to detect peaks of a voltage signal at the first LC tank, wherein the voltage signal reflects a voltage change induced by the second modulated signal; and
a first data demodulator configured to demodulate, based on the detected peaks, the sensing data carried by the voltage signal.

5. The apparatus of claim 2, wherein the internal device further comprises:
a clock recovery comparator configured to convert an analog signal at the second LC tank to a digital signal;
a second data demodulator configured to demodulate the control data based on the digital signal, wherein the digital signal serves as a clock signal for both the second data modulator and the second data demodulator; and a diode bridge rectifier configured to capture and store the power transmitted from the external device over the inductive link.

6. The apparatus of claim 1, wherein:
the external device is a wearable device; and
the internal device is an implantable medical device.

7. The apparatus of claim 1, wherein:
the switching power amplifier is one of: a class E amplifier or a class D amplifier.

8. A system, comprising:
an external device comprising:
a first LC tank comprising a first coil,
a class E amplifier comprising a first switch electrically coupled to the first LC tank, wherein the class E amplifier is configured to obtain a power carrier signal from an external power source, and
a first field programmable gate array (FPGA) configured to implement on-off keying (OOK) to open and close the first switch, wherein the first FPGA comprises a first data modulator configured to modulate the power carrier signal based on control data to generate a first modulated signal carrying both power and the control data, wherein the control data is encoded using OOK into the first modulated signal based on durations and positions of timed breaks of the first modulated signal; and
an internal device comprising:
a second LC tank comprising a second coil that is inductively coupled to the first coil through an inductive link, wherein the first modulated signal is transmitted from the external device to the internal device over the inductive link,
a tank circuit comprising a second switch electrically coupled to the second LC tank, and
a second FPGA configured to implement cyclic on-off keying (COOK) to open and close the second switch.

9. The system of claim 8, wherein:
the class E amplifier is configured to drive the first switch based on the first modulated signal.

10. The system of claim 8, wherein:
the tank circuit is configured to drive the second switch based on a second modulated signal.

11. The system of claim 10, wherein:
the second FPGA comprises a second data modulator configured to modulate sensing data to generate the second modulated signal carrying the sensing data;
the sensing data is encoded using COOK into the second modulated signal based on grounding both sides of the tank circuit for one cycle; and
the second modulated signal is transmitted from the internal device to the external device over the inductive link.

12. The system of claim 11, wherein:
the external device further comprises a data peak detector configured to detect peaks of a voltage signal at the first LC tank;
the voltage signal reflects a voltage change induced by the second modulated signal; and the first FPGA comprises a first data demodulator configured to demodulate, based on the detected peaks, the sensing data carried by the voltage signal.

13. The system of claim 11, wherein:
the internal device further comprises a clock recovery comparator configured to convert an analog signal at the second LC tank to a digital signal;
the second FPGA comprises a second data demodulator configured to demodulate the control data based on the digital signal, wherein the digital signal serves as a clock signal for both the second data modulator and the second data demodulator; and
a diode bridge rectifier configured to capture and store the power transmitted from the external device over the inductive link.

14. The system of claim 8, wherein:
the external device is a wearable device; and
the internal device is an implantable medical device.

15. A method, comprising:
obtaining a power carrier signal from a power source;
modulating the power carrier signal based on control data to generate a first modulated signal carrying both power and the control data, wherein the control data is generated at an external device and encoded using on-off keying (OOK) into the first modulated signal based on durations and positions of timed breaks of the first modulated signal;
transmitting the first modulated signal from the external device to an internal device over an inductive link;
modulating sensing data to generate a second modulated signal carrying the sensing data, which is generated at the internal device and encoded using COOK into the second modulated signal based on grounding both sides of a tank circuit in the internal device for one cycle;
transmitting the second modulated signal from the internal device to the external device over the inductive link.

16. The method of claim 15, wherein:
the external device comprises a first LC tank comprising a first coil; and
the internal device comprises a second LC tank comprising a second coil that is inductively coupled to the first coil through the inductive link.

17. The method of claim 16, further comprising:
obtaining an analog signal at the second LC tank;
converting the analog signal to a digital signal; and
demodulating the control data based on the digital signal.

18. The method of claim 17, further comprising:
capturing, from the analog signal, the power transmitted from the external device over the inductive link; and
storing the captured power at a battery in the internal device.

19. The method of claim 16, further comprising:
obtaining a voltage signal at the first LC tank, wherein the voltage signal reflects a voltage change induced by the second modulated signal;
detecting peaks of the voltage signal; and
demodulating, based on the detected peaks, the sensing data carried by the voltage signal.

* * * * *